(12) United States Patent
Somberg et al.

(10) Patent No.: US 7,923,447 B2
(45) Date of Patent: Apr. 12, 2011

(54) PARENTERAL SOLUTIONS CONTAINING METOLAZONE

(75) Inventors: John C. Somberg, Lake Forest, IL (US); Vasant V. Ranade, Libertyville, IL (US)

(73) Assignee: Academic Pharmaceuticals Incorporated, Lake Bluff, IL (US)

( * ) Notice: Subject to any disclaimer, the term of this patent is extended or adjusted under 35 U.S.C. 154(b) by 427 days.

(21) Appl. No.: 12/077,008

(22) Filed: Mar. 17, 2008

(65) Prior Publication Data

US 2009/0233951 A1 Sep. 17, 2009

(51) Int. Cl.
*A01N 43/58* (2006.01)
*A61K 31/50* (2006.01)

(52) U.S. Cl. ........................................ 514/247; 514/183

(58) Field of Classification Search .................... 514/183
See application file for complete search history.

(56) References Cited

U.S. PATENT DOCUMENTS

| 4,668,677 A * | 5/1987 | Morinaka et al. ............. 514/248 |
| 5,814,623 A * | 9/1998 | Ranade .......................... 514/155 |
| 2006/0034926 A1 * | 2/2006 | Fraatz et al. .................. 424/468 |

* cited by examiner

*Primary Examiner* — James D Anderson
*Assistant Examiner* — Meghan Finn
(74) *Attorney, Agent, or Firm* — Vance Intellectual Property, PC

(57) ABSTRACT

Disclosed herein are parenteral solutions containing 7-halo-1,2,3,4-tetrahydro-3-aryl-6-quinazoline sulfonamide in N,N-dimethylactamide, polyethylene glycol and $D_5W$ useful in the treatment of hypertension, heart failure and renal disease leading to edematous states. Also disclosed are methods for preparing such solutions.

17 Claims, 2 Drawing Sheets

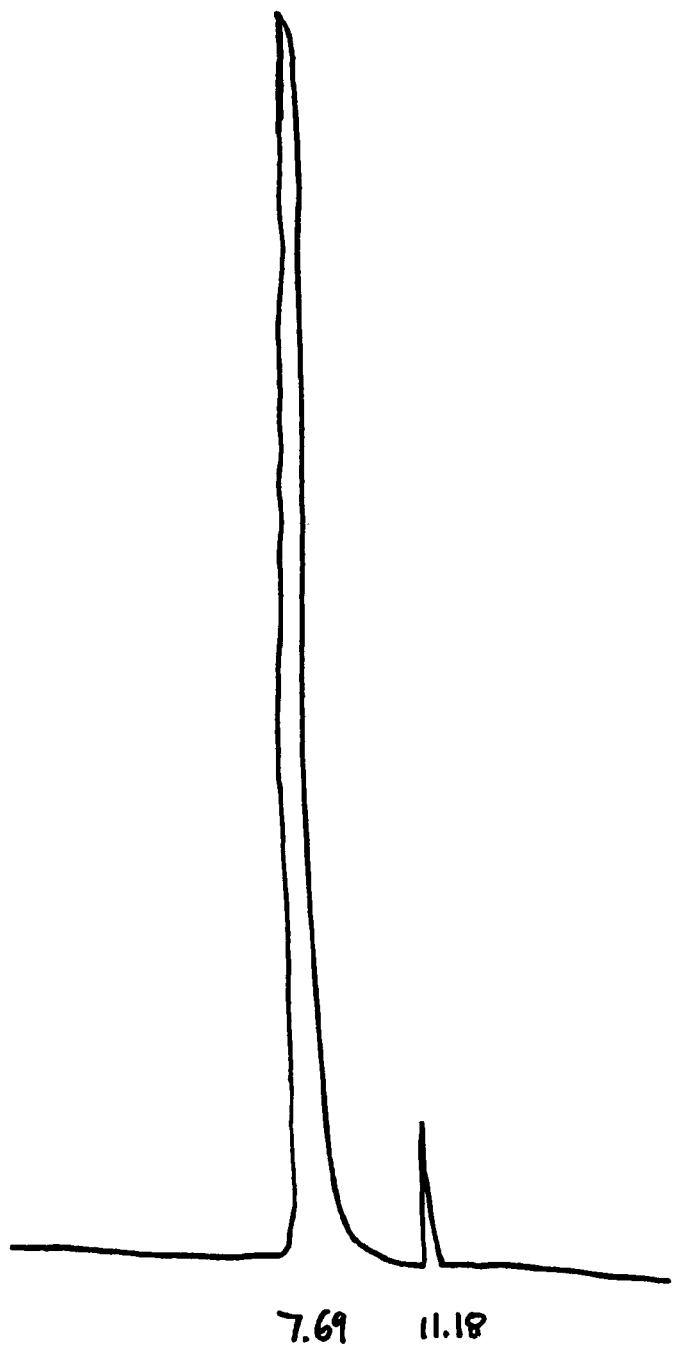
Fig 1: HPLC Chromatogram of 0.1 ml injection of metolazone in DMAC using a $C_{18}$ micro –Bondapak, column. Metolazone was found at rf 7.69 min, 99.5% purity at 6 months of stability testing at room temperature.

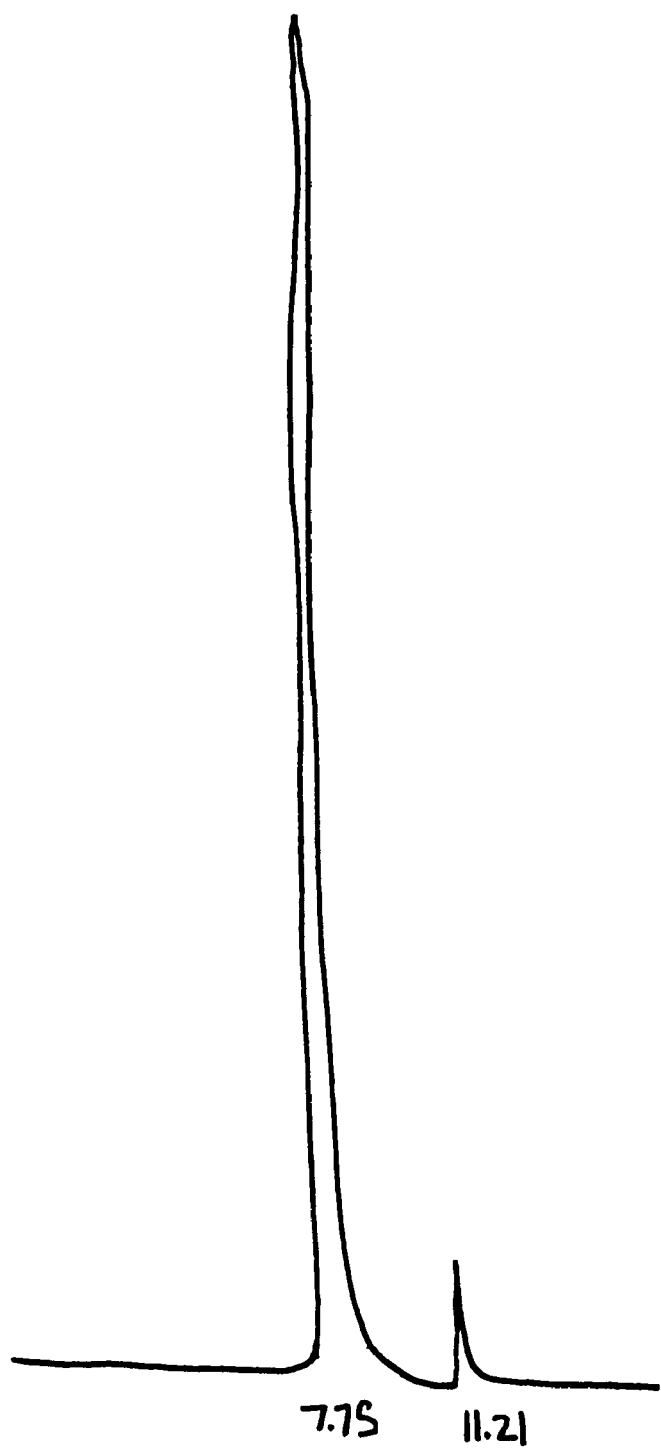
Fig 2: HPLC Chromatogram of 0.1 ml injection of metolazone in DMAC using a $C_{18}$ micro –Bondapak, column. Metolazone was found at rf 7.75 min, 99.6% purity at 6 months of stability testing at 40° C.

PARENTERAL SOLUTIONS CONTAINING METOLAZONE

BACKGROUND OF THE INVENTION

1. Field of the Invention

The present invention is related to parenteral solutions containing 7-Halo-1,2,3,4,-tetrahydro-3-aryl-6-quinazoline sulfonamides.

2. Description of the Related Art

Metolazone is a quinazoline diuretic approved for use in an oral tablet form (MYKROX) for the treatment of hypertension alone or in combination with other anti-hypertensive drugs of a different class. This compound acts primarily to inhibit sodium reabsorption at the cortical diluting site and to a lesser extent in the proximal convoluted tubule in the kidney. Sodium and chloride ions are excreted in approximately equivalent amounts. The increased delivery of sodium to the distal-tubular exchange site results in increased potassium excretion.

To treat hypertension, the compound may be administered in oral dosage forms such as in the form of a tablet containing from 0.5-10 mg of metolazone, or it may be administered in the form of an intravenous solution. Metolazone is also indicated for use in treating heart failure and renal disease. Further, when metolazone is combined with furosemide (lasix), the effectiveness of the diuretics is greatly enhanced. Furosemide can be administered intravenously to obtain the best and most rapid diuretic effect in emergencies. However, there is no intravenous formulation available of metolazone (at pH range of 6.8-8 and concentration ranging from 5 to 15 ml/mg) since metolazone is sparingly soluble in most solvents. Metolazone is only sparingly soluble in water, but is said to be somewhat more soluble in plasma, blood, alkali and organic solvents.

U.S. Pat. Nos. 3,360,518 and 3,557,111 disclose methods for preparing metolazone.

And previously, from this laboratory, we have disclosed methods for solubilizing metolazone in U.S. Pat. Nos. 5,633,240, 5,684,009 and 5,814,623.

Previous formulations used buffered alkaline solutions with a pH>9. The basic conditions used may cause degradation of metolazone, the active ingredient. Also it is not desirable to admix highly alkaline solutions with the body fluids (in vivo) as the resulting situation may cause deleterious effects such as irritation at the sight of injection or thrombosis.

BRIEF DESCRIPTION OF THE DRAWINGS

FIG. 1 is an HPLC chromatogram of metolazone in DMAC at 6 months of stability testing at room temperature.

FIG. 2 is an HPLC chromatogram at 6 months of stability testing at 40° C.

DESCRIPTION OF THE INVENTION

The present invention provides parenteral solutions comprising as an active ingredient a 7-Halo-1,2,3,4-tetrahydro-3-aryl-6-quinazoline sulfonamide of the following formula:

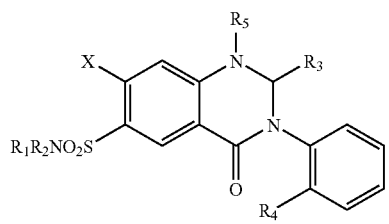

wherein X is a halogen:
$R_1$ $R_2$ $R_3$ and $R_4$ are independently selected from hydrogen and alkyl groups having from about 1 to 6 carbon atoms, and $R_5$ is hydrogen or an alkyl group having from about 1 to 6 carbon atoms.

More specifically, the present invention provides parenteral solutions suitable for intravenous administration containing as an active ingredient an effective antihypertensive amount of 7 chloro-1,2,3,4-tetrahydro-2-methyl-3-(-2-methylphenyl)-4-oxo-6-quinazoline sulfonamide (metolazone) in a sterile dipolar, aprotic co-solvent comprising, N,N-Dimethylacetamide (DMAC). This solvent, that is characterized by the presence of hydrogen-bonding-acceptors, such as nitrogen or oxygen atoms, but no donor groups, may dissolve a wide array of water insoluble materials. Solubilization by these type of solvents may be primarily due to their ability to disrupt intermolecular hydrogen bonding between water molecules. This chemical is included in the FDA approved "GRAS" list. Also included within the scope of the invention are methods for producing such solutions.

The invention provides solutions suitable for parenteral e.g. intravenous, administration comprising an effective antihypertensive amount of metolazone in an aqueous compatible, structurally similar other organic chemicals that contain amide or a polar moiety. In particular, the invention provides solutions suitable for parenteral administration comprising furosemide and metolazone in N,N-Dimethylacetamide (DMAC) at a pH ranging from 6.8-8. The amount of DMAC present in these formulations is within the acceptable limits proposed by the FDA (maximum concentration of 1.8%).

The invention also encompasses methods for treating patients suffering from or affected by edema or edematous states comprising parenteral, e.g. intravenous, administration of an effective amount of a solution of metolazone in an aqueous compatible solvent. Representative edematous states include, for example, congestive heart failure and hepatic or renal failure.

Parenteral solutions comprising metolazone according to this invention, are typically prepared by mixing the required amount of metolazone which may be purified prior to use in N,N-Dimethylacetamide and parenteral fluids such as D5W, distilled water, saline or PEG and adjusting the pH of this solution between 6.8-8. The process may be carried out at room temperature, or to increase concentration, the solution may be warmed appropriately (see example 1) Other solvents such as PEG 400, 600, polypropylene glycol or other glycols can be used to enhance solubility at pH approaching neutrality (see example 3). The resulting solutions after cooling to room temperature, may be sterilized by known means e.g. ultrafiltration using preferably 0.45 micron filter or ethylene oxide treatment or heating and may be packaged into ampules, vials or pre-filled syringes suitable for dispensing a sterile parenteral formulation.

The metolazone formulation in DMAC that is colorless and clear initially demonstrates remarkable stability when stored at room temperature and 40° C. over a period of 6 months without the formation of turbidity or a precipitate or a change in color and appearance.

This solution thus formulated is indicated for the treatment of edema secondary to heart failure, or renal disease. Solutions may also be prepared in a similar manner to contain furosemide and metolazone. The dosage must be individualized by the treating clinician to optimize safe diuresis.

One skilled in the art will recognize that modifications may be made in the present invention such as increasing concentration of DMAC and pH (>8, more basic) in order to achieve greater concentration of metolazone per ml of the diluent without deviating from the spirit or scope of the invention. The invention is illustrated further by the following examples which are not to be construed as limiting the invention or scope of the specific procedures described herein.

Example 1

To 50 mg of metolazone and 0.1 ml of DMAC was added 9.9 ml of 5% dextrose solution. The mixture was kept in a water bath at 50° C. while stirring and pH of this suspension was adjusted to 7.5-8 with dilute NaOH solution. The mixture was stirred and cooled to room temperature when a clear solution was obtained. It was then filtered thought a Millipore filter (0.45 microns) and stored at RT and 40° C. After a period of 6 months at RT and 40° C., the solutions remained clear and colorless and no turbidity or change in color was apparent. The results of this example demonstrated the stability of metolazone in this formulation that contains 1% DMAC. HPLC results (see FIGS. 1 and 2) indicate the stability of metolazone in this formulation.

Example 2

In another example, 50.0 mg of metolazone and 0.2 ml of DMAC was added 9.8 ml of 5% dextrose solution. The mixture was stored at room temperature and pH of this solution was adjusted to 7.5-8 with dilute NaOH solution. It was then filtered through a Millipore filter (0.45 μm) and stored at RT and 40° C. After a period of 6 months at RT and 40° C., the solutions remained clear and colorless and no turbidity or development of color was apparent.

Example 3

To 150.0 mg of metolazone and 0.1 ml of DMAC was added 9.9 ml of polyethlylene glycol 300 (400 or 600). The mixture was kept in a water bath at 40-50° C. while stirring and pH of this suspension was adjusted to 6.8. Mixture was stirred and cooled to room temperature when a clear solution was obtained. (This solution can be diluted at a ratio of 65:35 with $D_5W$, saline or distilled $H_2O$ without any turbidity or precipitation). It was then filtered through a Millipore filter (0.45 μm) and stored at RT and 40° C. After a period of 6 months at RT and 40° C., the solutions remained clear and colorless and no turbidity or development of color was apparent. The results of these examples demonstrate the stability of metolazone in this formulation that contains 1% DMAC. Stability testing results (see Table 1) for examples 2 and 3 indicate stability of metholazone in this formulation.

From the foregoing discussion it will be appreciated that, although specific embodiments of the invention have been described herein for purposes of illustration, various modifications may be made without deviating from the spirit and scope of the invention.

TABLE 1

Results of Stability Testing

|  | RT | 40° | Results |
|---|---|---|---|
| EXAMPLE 1 | 6 mo | 6 mo | Samples clear, colorless* |
| EXAMPLE 2 | 6 mo | 6 mo | Samples clear, colorless |
| EXAMPLE 3 | 6 mo | 6 mo | Samples clear, colorless |

*See FIG. 1 and 2 HPLC chromatograms

High Pressure Liquid Chromatography of Metolazone Solution Formulation

For liquid chromatography, $C_{18}$ μ-Bondapak column was used. The UV detector was set at 235 nm and the flow rate was 1 ml/min. The mobile phase consisted of buffer solution containing 1.38 gm or monobasic potassium phosphate monohydrate in 900 ml of water, pH adjusted to 3.0 with phosphoric acid and diluted to 1 liter with water. The mobile solvent system contained the above described phosphate buffer, methanol and acetonitrile (65:28:7 v/v/v/). The metolazone formulation solutions that were stored at RT and 40° for a period of 6 months were subjected to the LC analysis. In the FIGS. 1 & 2 the chromatography of the analysis indicated the peak of metolazone at retention times of 7.69/7.75 minutes. The purity of this analysis indicated >99%.

Example 4

To 150 mg of metolazone and 0.1 ml DMAC was added 9.9 ml of polypropylene glycol. The mixture was kept in a water bath at 40-50° C. while stirring and pH of this solution was adjusted to 6.8. Mixture was stirred and cooled to room temperature when a clear, colorless solution was obtained. This solution can be diluted (65:35) with $D_5W$, saline or distilled $H_2O$ without any turbidity, precipitation or change in color or appearance.

Evaluation of the Diuretic Action of Parenteral Formulations of Metolazone

Intraperitoneal Administration in Rats

Sprague-Dawley male rats (400 to 500 g) were used for the in vivo experiments. The rats were housed at a controlled temperature (22° C.), fed regularly and had free access to water.

Experimental Sequences

Rats were divided into 7 groups with 6 animals per group for the purposes of the study. The rats were deprived of food and water for 24 hours before beginning the study. After this fasting period, normal saline (25 mg/kg) was given by oral route. One group received only 1 mL of saline administered introperitoneally. A second group received 2 mg/kg metolazone in 1 mL of the Tris formulation administered introperitoneally. A third group received 2 mg/kg metolazone in 1 mL of lipid formulation administered intraperitoneally. The fourth, fifth, and sixth groups received 2, 4, and 6 mg/kg furosemide, respectively, in 1 mL normal saline administered intraperitoneally. A seventh group received 4 mg/kg furosemide plus 2 mg/kg metolazone in 1 mL of the new formulation administered intraperitoneally. All rats were placed in metabolic cages for urine collection. Urine was collected for 24 hours after injection, and the volume measured and the ($Na^+$) concentration in urine were determined using an ion-specific electrode method, NOVA CRT (NOVA Biomedical, Waltham, Mass.)

Statistical Analysis

All data are presented as mean±SD of n observations. For statistical comparison, one-way analysis or variance ANOVA or Student t test was employed. A two-sided P value≦0.05 was considered significant.

Results

The urine volume voided over 24 hours was significantly greater in rats receiving furosemide than those receiving placebo (P≦0.01) greater at each increment in concentration of 2, 4, 6, mg/kg furosemide, respectively. Following administration of the 2 different formulations of metolazone, the urine volume collected for 24 hours was greater in each instance when compared with placebo. When 2 mg/kg metolazone and 4 mg/kg furosemide were combined and injected intraperitoneally, a higher urine volume was obtained over 24 hours after injection of 4 mg/kg furosemide (P≦0.05) or 2 mg/kg metolazone (P≦0.01) given separately.

The concentration of urinary $Na^+$ was measured in the collected urine after the injection of 2 mg/kg metolazone and the injection of different concentrations of furosemide (2, 4, and 6 mg/kg). The combination of 4 mg/kg furosemide in 0.5 mL of saline and 2 mg/kg metolazone in 0.5 mL of new formulation buffer produced a natriuresis that was significantly greater than with placebo (normal saline) administration (P≦0.01) or each agent administrated separately.

Summary of Results

Vehicle (Tris buffer) caused 9±mL/d output of urine with a sodium [$Na^+$] concentration of 194±41 μmol/L (n=6 per group). Metolazone 2 mg/kg resulted in 16±3 mL/d urine output and sodium [$Na^+$] of 278±76 μmol/L (n=6 per group). Furosemide 2, 4, and 6 mg/kg resulted in a volume of urine 9±1, 14±2 and 17±2 mL/d and [$Na^+$] μmol/L of 194±41, 206±108, and 229±91, respectively. Metolazone (new formulation) 4 mg/kg combined with furosemide 4 mg/kg resulted in a urine volume of 21±1 mL/d and [$Na^+$] of 326±108 μmol/L.

It can be concluded from these results that combining metolazone and furosemide can cause an increase in urine volume and sodium excretion. Therefore, metolazone administrated parenterally in combination with the parenteral administration of furosemide appears to have an important clinical potential.

What is claimed is:

1. A solution suitable for parenteral administration, comprising: 1 to 15 mg/mL metolazone dissolved in up to 2% by volume N,N-dimethylacetamide (DMAC) and the reminder of the solution being 5% dextrose ($D_5W$), wherein the pH of the solution is from 6.8-8.

2. The solution of claim 1, wherein the pH of the solution is from 7.5-8.

3. The solution of claim 1, wherein the metolazone is dissolved in 1% by volume DMAC, and the remainder being $D_5W$.

4. The solution of claim 1, wherein the metolazone is dissolved in 2% by volume DMAC, and the remainder being $D_5W$.

5. The solution of claim 1, wherein 5 mg/mL of metolazone is present.

6. The solution of claim 1, wherein 15 mg/mL of metolazone is present.

7. The solution of claim 1, wherein 5 mg/mL of metolazone is present and dissolved in 1% by volume DMAC and the remainder being $D_5W$.

8. The solution of claim 7, wherein the pH is 7.5-8.

9. The solution of claim 1, wherein 15 mg/mL of metolazone is present and dissolved in 1% by volume DMAC and the remainder being $D_5W$.

10. The solution of claim 9, wherein the pH is 7.5-8.

11. The solution of claim 1, wherein 5 mg/mL of metolazone is present and dissolved in 2% by volume DMAC and the remainder being $D_5W$.

12. The solution of claim 11, wherein the pH is 6.8.

13. A method of treating hypertension, comprising: parenterally administering a therapeutically effective amount of a solution, comprising: 1 to 15 mg/mL metolazone dissolved in up to 2% by volume N,N-dimethylacetamide (DMAC) and the reminder of the solution being 5% dextrose ($D_5W$), wherein the pH of the solution is from 6.8-8.

14. The method of claim 13, wherein the pH of the solution is from 7.5-8.

15. The method of claim 13, wherein 5 mg/mL of metolazone is present and dissolved in 1% by volume DMAC and the remainder being $D_5W$ and the pH is 7.5-8.

16. The method of claim 13, wherein 15 mg/mL of metolazone is present and dissolved in 1% by volume DMAC and the remainder being $D_5W$ and the pH is 7.5-8.

17. The method of claim 13, wherein 5 mg/mL of metolazone is present and dissolved in 2% by volume DMAC and the remainder being $D_5W$ and the pH is 6.8.

* * * * *